United States Patent [19]

Vogel et al.

[11] Patent Number: 5,610,175
[45] Date of Patent: Mar. 11, 1997

[54] 9-SUBSTITUTED PORPHYCENES

[75] Inventors: Emanuel Vogel; Martin Mueller, both of Cologne, Germany; Otto Halpern, Gerona, Spain; Alexander D. Cross, Atherton, Calif.

[73] Assignee: Cytopharm, Inc., Menlo Park, Calif.

[21] Appl. No.: 418,118

[22] Filed: Apr. 6, 1995

[51] Int. Cl.$^6$ .................... A61K 31/40; C07D 487/22
[52] U.S. Cl. ............................ 514/410; 540/145
[58] Field of Search .............. 514/410; 424/450; 540/145

[56] References Cited

U.S. PATENT DOCUMENTS

| | | | |
|---|---|---|---|
| 3,592,930 | 7/1971 | Katz et al. | 424/243 |
| 3,989,816 | 11/1976 | Rajadhyaksha | 424/60 |
| 3,991,203 | 11/1976 | Rajadhyaksha | 424/274 |
| 4,017,615 | 4/1977 | Shastri et al. | 424/241 |
| 4,411,893 | 10/1983 | Johnson et al. | 424/181 |
| 4,448,765 | 5/1984 | Ash et al. | 424/14 |
| 4,452,747 | 6/1984 | Gersonde et al. | 264/4.1 |
| 4,721,612 | 1/1988 | Janoff et al. | 424/1.1 |
| 4,837,028 | 6/1989 | Allen | 424/4.5 |
| 4,861,876 | 8/1989 | Kessel | 540/145 |
| 4,913,907 | 4/1990 | Jori et al. | 424/450 |
| 4,957,481 | 9/1990 | Gatenby | 604/20 |
| 4,961,920 | 10/1990 | Ward | 424/9 |
| 5,015,478 | 5/1991 | Jori et al. | 424/450 |
| 5,132,101 | 7/1992 | Vogel et al. | 514/410 |
| 5,179,120 | 1/1993 | Vogel et al. | 424/9 |
| 5,244,671 | 9/1993 | Vogel et al. | 514/450 |
| 5,262,401 | 11/1993 | Vogel et al. | 514/32 |
| 5,286,474 | 2/1994 | Gust, Jr. et al. | 424/7.1 |
| 5,409,900 | 4/1995 | Vogel et al. | 514/17 |

OTHER PUBLICATIONS

Vogel et al, *Pure & Appl. Chem.*, 62(3), 557 (1990).
Richert et al, *Photodynamic Therapy in Biomedical Lasers*, P. Spinelli, M. Dal Fante, R. Marchensini (Eds.) Excerpta Medica 1011, 702; Elsevier, Amsterdam (1992).
Vogel et al, *Angew. Chem. Int. Ed. Engl.*, 25, 257 (1986).
Aramendia et al, *Photochem. Photobiol.*, 44, 555 (1986).
Jux et al, *Angew. Chem. Int. Ed. Engl.*, 29, 1385 (1990).
Vogel et al, *Angew. Chem. Int. Ed. Engl.*, 29, 1387 (1990).
Will et al, *Angew. Chem. Int. Ed. Engl.*, 29, 1390 (1990).
Milanesi et al, *Lasers in Med. Science*, 6, 437 (1991).
Szeimies et al, *Photochemistry and Photobiology*, 59(1), 73 (1994).
Gamarra et al, *Photodynamic Therapy and Biomedical Lasers*, P. Spinelli, M. Dal Fante, R. Marchensini (Eds.) Excerpta Medica 1011, 706; Elsevier, Amsterdam (1992).
Leunig et al, *Brit. J. Cancer*, 68, 225 (1993).
Aicher et al, *Optical Engineering*, 32, 342 (1993).
Richert, *J. Photochem. Photobiol. B:Biology*, 19, 67 (1993).
Schaffner et al, *Biologic Effects of Light*, 312 (1993); E. Jung, M. F. Holick (Eds.); Walter de Gruyter, Berlin, New York (1994).
Richert et al, *J. Med. Chem.*, 37, 2797 (1994).
Berger et al, *Tetrahedron Letters*, 44, 4225 (1978).
Dougherty et al, *Cancer Research*, 38, 2628 (1978).
Dellian et al, *Photodynamic Therapy and Biomedical Lasers*, P. Spinelli, M. Dal Fante, R. Marchensini (Eds.) Excerpta Medica, 1011, 467; Elsevier, Amsterdam (1992).
Kimel et al, *Proc. Photodynamic Therapy of Cancer*, SPIE, 2078, 205 (1994).
Nonell et al, *J. Photochem. Photobiol.*, 51, 551 (1990).
Martire et al, *J. Am. Chem. Soc.*, 114, 9969 (1992).

*Primary Examiner*—Mukund J. Shah
*Assistant Examiner*—Pavanaram K. Sripada
*Attorney, Agent, or Firm*—Oblon, Spivak, McClelland, Maier & Neustadt, P.C.

[57] ABSTRACT

Porphycene compounds having the formula

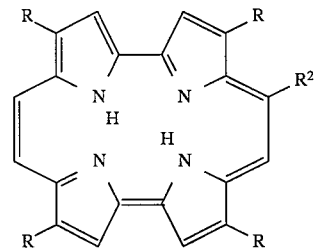

wherein each R is —$(CH_2)_n$—X, n=1–10, X is $OR^1$ and $R^1$ is alkyl, aralkyl or aryl are useful as photosensitizer compounds in photodynamic therapy.

18 Claims, No Drawings

9-SUBSTITUTED PORPHYCENES

BACKGROUND OF THE INVENTION

1. Field of the Invention

The invention relates to novel porphycene compounds and pharmaceutical compositions containing these compounds which are useful for therapeutic treatment.

2. Discussion of the Background

During the past few years there has developed a widespread recognition that modern, though sophisticated, cancer diagnosis and treatments have served neither to reduce overall the number of cases of reported cancers in the U.S.A. nor, save the notable cases, the death rate. This is a disheartening result for the billions of dollars invested in conquering the disease. Moreover, surgery, radiotherapy and chemotherapy are all associated with major debilitating side effects such as trauma, severe immunosuppression or toxicity which are not easily surmounted by patients already compromised by ill-health.

Early work in the 1970's, followed by rapidly expanding studies in the 1980's, has shown that photodynamic therapy (PDT) offers a viable, less toxic and generally less painful avenue to treatment of cancer. Not all cancers are candidates for PDT. However, neoplasms of hollow organs and skin, including multifocal carcinoma in situ, sometimes inoperable, and with no good track record for treatment by established therapeutic procedures, appear to be targets for PDT.

In photodynamic therapy, porphyrinoid dyes are administered to a patient and localize in neoplastic tissues (Lipson et al., J. Thoracic Cardiovascular Surgery, 1961, 42:623–629). Irradiation of the porphyrinoid dye with light at a wavelength which corresponds to an absorption band of the dye results in destruction of the neoplastic tissue. See also Kessel, D., "Methods in Porphyrin Photosensitization", Plenum Press, New York, 1985; Gomer, C. J., "Photodynamic Therapy", Pergammon Press, Oxford, 1987 and Doiron, D. R. and Gomer, C. J., "Porphyrin Localization and Treatment of Tumors", Liss, New York, 1984. The use of a fiber optic laser light source is described in U.S. Pat. No. 4,957,481.

Dougherty et al. (Cancer Res., 1978, 38:2628; Photochem. Photobiol, 1987, 45:879) pioneered the field with infusion of photoactivatable dyes, followed by appropriate long wavelength radiation of the tumors (600+nm) to generate a lethal shortlived species of oxygen which destroyed the neoplastic cells. Early experiments utilized a mixture termed hematoporphyrin derivative (HPD). See also Lipson et al., J.N.C.I., 1961, 26:1; Dougherty et al., J.N.C.I., 1975, 55:115; Diamond et al., Lancet, 1972(II), 1175; D. Dolphin, "The Porphyrin", vol. I, Academic Press, New York, 1978; and D. Kessel, Photochem. Photobiol., 1984, 39:851. The deficiencies of HPD, especially prolonged phototoxicity caused by retained HPD components in human skin led to its displacement by a purified fraction initially termed dihematoporphyrin ether (DHE), and later marketed by QuadraLogics Technologies as the commercial product "PHOTOFRIN", which, although yielding improvements over HPD, nevertheless still suffered certain practical limitations. Relatively weak absorption in the wavelength range above 600 nm, retention in dermal cells (potentially leading to phototoxicity), only modest or low selectivity for tumor cells versus other cell types in vital organs, the inability to use available, modern, inexpensive diode lasers, and uncertain chemical constitution of the mixtures are all known negative features of PHOTOFRIN and HPD. The great majority of the earlier PDT agents studied have been derived from natural sources (porphyrin, chlorins, purpurins, etc.) or from known chemicals originating in the dyestuffs industry (e.g., cyanine dyes). For more recent PDT agents derived from natural sources see U.S. Pat. No. 4,961,920 and U.S. Pat. No. 4,861,876.

In animal and cell culture experiments one observes, following PDT, depending on the incubation time, damage to the vasculature, cell membranes, mitochondria and specific enzymes. When absorbed in tumor cells, an increased selectivity can be obtained by injecting the porphyrinoid sensitizers enclosed in liposomes (Ricchelli and Jori, Photochem. Photobiol., 1986, 44:151). Porphyrinoid dyes can be transported in the blood with the aid of lipoproteins such as low-density lipoprotein (Jori et al., Cancer Lett., 1984, 24:291).

PDT has been used to treat bladder, bronchial, bone marrow and skin tumors (Dougherty, Photochem. Photobiol., 1987, 45:879, Sieber et al., Leukemia Res., 1987, 11:43) as well as severe psoriasis (Diezel et al., Dermatol. Monatsschr., 1980, 166:793; Emtenstam et al., Lancet, 1989 (I), 1231). Treatment of viruses in transfused blood has also been reported (Matthews et al., Transfusion, 1988, 28:81; Sieber et al., Semin. Hematol., 1989, 26:35).

As the deficiencies of earlier PDT agents have become apparent, it also becomes possible to define activity parameters for improved chemically pure photoactivatable dyes for PDT therapy, available by chemical synthesis. Moreover, the products of synthesis lend themselves more readily to further chemical structural manipulation than do the naturally occurring starting materials which can be expensive and bear chemically sensitive constituents. The synthesis of novel porphycene macrocycles embracing four pyrrole rings has been described by Vogel and coworkers. Alkylated porphycenes have also been prepared (R=Me, Et, n-Pr, tert. butyl, phenyl) and the photochemical properties determined. The potential suitability of these compounds for PDT was noted and confirmed in animal studies (Guardiano et al., Cancer Letters, 1989, 44, 1).

Synthetic efforts have focused on porphyrinoid compounds which are highly absorptive in the longer wavelength range of about 600–900 nm, where the transparency of tissue is higher. Compounds such as purpurines (Morgan et al., J. Org. Chem., 1986, 51:1347; Morgan et al., Cancer Res., 1987, 47:496; Morgan et al., J. Med. Chem., 1989, 32:904; Hoober et al., Photochem. Photobiol., 1988, 48:579), naphthocyanin silicon complexes (Firey et al., J. Am. Chem. Soc., 1988, 110:7626), chlorins (Robert et al., J.N.C.I., 1988, 80:330; Kessel, Cancer Res., 1986, 46:2248), bacteriochlorins (Beams et al., Photochem. Photobiol., 1987, 46:639) and substituted phenylporphyrins (Kreimer-Birnbaum, Semin. Hematol., 1989, 26:157) have been prepared and tested in vivo. Additional PDT agents are described in EP 276,121.

Pyrrole-containing ring systems larger than porphycene have also been prepared and evaluated as photosensitizers. Sessler et al. have prepared and studied texaphyrin (J. Am. Chem. Soc., 1988, 110:5586) and Woodward et al. and Johnson et al. have prepared and investigated the sapphyrin ring system. Additionally, the platyrin system has been studied by LeGoff (Tetrahedron, Lett., 1978, 4225; J. Org. chem., 1987, 710) and vinylogous porphyrins have been studied by Franck (Angew. Chem., 1986, 98:1107; Angew. Chem. Int. Ed. Eng., 1986, 25:1100; Angew. Chem., 1988, 100:1203; Angew. Chem. Int. Ed. Eng., 1988, 27:1170).

A need continues to exist, therefore, for new compounds for use in PDT therapy, which compounds are easily available, have low intrinsic toxicity, are efficient photosensitizers for singlet oxygen production, have selective uptake in rapidly proliferating cells, are rapidly or at least moderately rapidly degraded and eliminated from the tissues after administration and which are available as chemically pure and stable compounds easily subject to synthetic modification. The compound should be capable of formulation to allow transdermal delivery if targeted for topical application.

SUMMARY OF THE INVENTION

Accordingly, one object of the present invention is to provide new and effective compounds for use in photodynamic therapy whose properties and characteristics approach the ideal characteristics of PDT dyes listed above.

This and other objects which will become apparent from the following specification have now been achieved with the compounds of the present invention. The present compounds have utility as PDT dyes for use in cancer therapy and dermatological diseases, i.e., psoriasis, etc.

DETAILED DESCRIPTION OF THE PREFERRED EMBODIMENTS

The porphycene compounds of the present invention have the structure shown below.

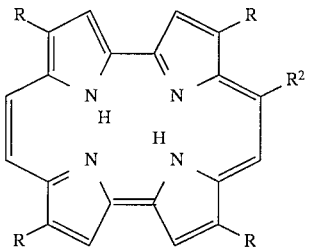

In this structure each R in the 2, 7, 12, and 17-positions of the porphycene structure is, independently of one another, $-(CH_2)_n-X$ where $n=1-10$, X is $OR^1$, and $R^1$ is alkyl, aralkyl or aryl.

In the structure shown above, $R^2$ may be hydroxy or alkoxy, preferably $C_{1-10}$ alkoxy.

Alternatively, $R^2$ may be $-OC(O)R^3$, where $R^3$ is $-(CH_2)_m-Y$, $m=1-10$, preferably 1-6, and Y is:

(a) hydrogen or halogen (F, Cl, Br, I), (b) $COOR^4$, where $R^4$ is hydrogen, alkyl, aryl, aralkyl, cycloalkyl or cycloalkylalkyl, (c) $NR^5R^6$, where $R^5$ and $R^6$ independently, are hydrogen, alkyl, aryl, aralkyl, cycloalkyl or cycloalkylalkyl, or $R^5$ and $R^6$ taken together with the nitrogen atom to which they are attached are a 3-7 membered saturated or unsaturated heterocyclic ring optionally containing an additional O, $NR^4$ or S ring member, and $R^4$ is as defined above, (d) $NR^4R^5R^{6+}\ A^-$, where $A^-$ is an anion and $R^4R^5$ and $R^6$ are as defined above, (e) $NH-C(O)OR^4$, where $R^4$ is as defined above.

In further embodiments, $R^2$ may be $-OC(O)R^7$, where $R^7$ is $-CHR^8=CHR^9-R^{10}$, $R^8$ and $R^9$ are, independently, hydrogen or $C_{1-6}$ alkyl and $R^{10}$ is alkyl, cycloalkyl, cycloalkylalkyl, aralkyl or aryl. $R^7$ may also be an aryl group, unsubstituted or having 1-3 substituents including halogen, haloalkyl, nitro, cyano, $C_{1-6}$ alkyl, $C_{1-6}$ alkoxy and $C_{2-6}$ alkoxycarbonyl.

In another embodiment $R^2$ may be $NR^{11}R^{12}$, where $R^{11}$ and $R^{12}$, independently, are hydrogen, alkyl, aryl, aralkyl, cycloalkyl or cycloalkylalkyl groups. $R^2$ may also be a $NHCO-(CH_2)_p-Z$, $NHCO-O(CH_2)_p-Z$ or $NH(CH_2)_{p+1}-Z$ group, where $p=1-10$, preferably 1-6, and Z is H, OH, $NR^{11}R^{12}$, $C(O)OR^4$, $OC(O)R^4$, $C(O)NHR^4$ or $NHC(O)OR^4$, where $R^4$ is as defined above.

The compound 9-acetoxy-2,7,12,17-tetrakis(methoxyethyl) porphycene is not within the scope of the present invention.

To improve water solubility, the porphycene compounds may be further bonded to amino acids, peptides, monosaccharides or oligosaccharides. Generally, the porphycene compounds are bonded to an amino acid or peptide through a free hydroxyl, amino or carboxy group using conventional condensation reactions. Similarly, the porphycenes may be bonded to glycosides using well known chemistry. Additionally, the porphycene compounds may be bonded to carotenoids to provide compounds which fluoresce and are useful as tumor diagnostic agents.

Suitable alkyl groups within this invention are straight-chain or branched alkyl groups. Preferably, the alkyl groups have 1-10 carbon atoms, more preferably 1-6 carbon atoms. Examples include methyl, ethyl, n-propyl, i-propyl, n-butyl, i-butyl, t-butyl, n-pentyl, ethylhexyl, decyl, etc.

Suitable cycloalkyl groups include cycloalkyl groups having 3-7 ring atoms, preferably cyclopropyl, cyclopentyl, cyclohexyl and cycloheptyl groups. These cycloalkyl groups may be unsubstituted or may be substituted with one or more alkyl substituents, generally from 1 to 3 alkyl groups having 1-6 carbon atoms.

Suitable cycloalkylalkyl groups include the cycloalkyl groups described above bonded to a straight-chain or branched alkyl group, preferably an alkyl group having 1-10 carbon atoms.

Suitable aryl groups include $C_{6-20}$ carbocyclic aryl groups, optionally substituted, preferably with one or more $C_{1-6}$ alkyl groups. Examples include phenyl, naphthyl, indenyl, etc. Arylene groups ($C_6H_4$) may be ortho-, meta- or para- substituted, preferably para-substituted.

Suitable aralkyl groups are the aryl groups defined above bonded to a $C_{1-6}$ alkylene group. Examples include benzyl, phenylethyl, phenylpropyl, phenylbutyl, etc.

Suitable amino acids are the 20 naturally occurring amino acids, i.e., phenylalanine, leucine, serine, tyrosine, alanine, glycine, cysteine, tryptophan, proline, histidine, arginine, glutamine, isoleucine, methionine, threonine, asparagine, lysine, valine, aspartic acid, glutamic acid. Suitable peptides include two or more of these amino acids, preferably 2-10, more preferably 2-6 amino acids bonded together through amide bonds.

Monosaccharides which may be bonded to the porphycene compounds of the present invention include both pentose and hexose saccharides including glucose, mannose, galactose, fructose, etc. Similarly, oligosaccharides containing a plurality of monosaccharide units, preferably 2-6 saccharide units, more preferably 2-3 saccharide units may be bonded to the porphycene compound.

Suitable carotenoid substituents have the structure (III) shown below.

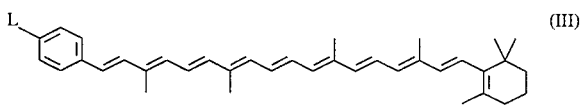

In this structure, L is a linking group through which the carotenoid substituent is bonded to the porphycene ring structure. Suitable linking groups L include —OC(O)— and —NHC(O)—.

Particularly, preferred compounds contain four identical R substituents. In these preferred compounds, R is —$(CH_2)_n$—$OR^1$ where $R^1$ is $C_{1-6}$ alkyl and $n=1-6$.

Preferred substituents $R^2$ are OH and $OCOR^3$, where $R^3$ is —$(CH_2)_m$—Y, $m=1-6$ and Y is halogen (preferably Cl or Br), $COOR^4$ where $R^4$ is $C_{1-6}$ alkyl, $NH_2$ and $NHC(O)OR^4$ where $R^4$ is $C_{1-6}$ alkyl. Additional preferred substituents $R^2$ are —$NHCO(CH_2)_p$—Z where $p=1-6$ and Z is OH, $NH_2$, COOH, or $OCOR^4$ where $R^4$ is $C_{1-6}$ alkyl.

Also preferred are compounds in which $R^3$ is —$C_6H_4$—$OR^4$ or —$C_6H_4$—$C(O)OR^4$, where $R^4$ is an alkyl group having 1-6 carbon atoms. When $R^7$ is —$CR^8$=$CR^9$—$R^{10}$, $R^8$ and $R^9$ are preferably hydrogen and $R^{10}$ is preferably phenyl. The phenyl group may be unsubstituted or substituted with 1-5, preferably 1-2 $C_{1-6}$ alkyl groups, preferably straight-chain alkyl groups.

The anion $A^{31}$ may be any pharmaceutically acceptable anion including, but not limited to inorganic anions such as chloride, sulfate, phosphate, diphosphate, bromide and nitrate and organic anions such as acetate, malate, maleate, fumarate, tartrate, succinate, citrate, lactate, methanesulfonate, p-toluenesulfonate, palmoate, salicylate and stearate.

The tetrasubstituted porphycenes are prepared by coupling appropriately substituted dialdehydes to form the porphycene ring structure and further modification of the resulting tetrasubstituted porphycene. Synthesis of suitable tetrasubstituted porphycene starting materials are described in U.S. Pat. No. 5,179,120. This patent is incorporated herein by reference in its entirety to provide a more complete description of how to prepare suitable tetrasubstituted porphycenes.

Acyloxy compounds of the present invention may be prepared by reacting a suitable porphycene precursor having the formula (I)

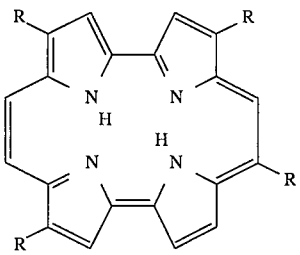

with an organic acid of the formula (II)

$R^7$—COOH or $R^3$—COOH (II)          (II)

where $R^3$ and $R^7$ are as defined above, in the presence of lead oxide ($PbO_2$) or manganese oxide ($MnO_2$) The reaction is generally conducted in organic aprotic solvents such as halogenated hydrocarbons (e.g., chloroform, methylene chloride) or acetonitrile. The tetrasubstituted porphycene precursor is stirred with the lead oxide or manganese oxide for a period of time sufficient to complete the reaction forming compounds of the invention in which $R^2$ is $OC(O)R^3$ or $OC(O)R^7$. Generally, about equimolar amounts of the starting tetrasubstituted porphycene and the lead oxide or manganese oxide are combined together with a slight excess of the organic acid in the solvent and stirred at room temperature. The specific reaction time depends upon the acid used and whether or not lead oxide or manganese oxide is used. Reactions with lead oxide are generally faster than the corresponding reactions with manganese oxide. Reaction times ranging from about 20 minutes to about 10 weeks are generally necessary to produce the desired 9-substituted products. The resulting reaction mixture is then poured into a dilute aqueous base solution, e.g. aqueous $NaHCO_3$, and may be purified by extraction, chromatography, recrystallization, etc. according to known procedures.

Terminal amides and esters in $R^3$ can be selectively hydrolysed to the corresponding amine or carboxylic acid using appropriate conventional acid hydrolysis conditions. Compounds of the present invention in which $R^2$ is —$OR^3$ are prepared by alkylating the corresponding compound in which $R^2$ is hydroxy using known alkylating reactions. Suitable alkylating reagents include dialkylsulfates, i.e. dimethylsulfate, and alkyl halides. The hydroxy compounds are available by hydrolysis of the corresponding acyloxy compounds.

The compounds of the present invention in which $R^2$ is —NHCO—$(CH_2)_p$—Z are prepared by reacting the tetrasubstituted porphycene precursor identified above with silver nitrate and acetic acid to form the corresponding nitro tetrasubstituted porphycene. The nitro derivative is then reduced with sodium dithionite/sodium hydroxide to produce the corresponding amino derivative. Suitable synthetic procedures are described in U.S. Pat. No. 5,244,671 which is incorporated herein by reference in its entirety. The 9-amino-porphycene can be reacted with an acid halide having the formula Hal-CO—$(CH_2)_p$—Z where Z is $C(O)OR^4$ or $C(O)NHR^4$. This reaction is generally conducted in a polar aprotic solvent such as tetrahydrofuran (THF) containing a base such as pyridine. The terminal ester or amide group may be selectively hydrolyzed to the corresponding carboxylic acid by alkaline or acid hydrolysis, e.g. $NaOH/CH_3OH/THF$ or $NaOCH_3/CH_3OH/THF$. The terminal ester group may also be reduced to the corresponding alcohol using, for example, a metal hydride reduction (e.g. $LiAlH_4/THF$ or $LiBH_4/THF$).

The compounds of the present invention in which $R^2$ is —$NH(CH_2)_{p+1}$—Z can be prepared by reducing the carbonyl of the —$NHCO(CH_2)_p$—Z group using conventional reduction reactions.

Porphycene compounds bonded to amino acids, proteins, monosaccharides or oligosaccharides are prepared using known reactions. See U.S. Pat. No. 5,244,671, incorporated herein by reference.

Carotenoid derivatives of the porphycene compounds of the present invention are prepared by forming carotenoid compounds in which L is an acid halide, for example an acid chloride, having a structure Cl—C(O)— and reacting the carotenoid acid halide with a porphycene having a hydroxy or amino group at the 9-position.

Metal complexes containing divalent metals, preferably complexes of smaller metals such as zinc, nickel, magnesium, tin, etc., and the porphycene compounds of the present invention can be easily prepared by the addition of metal salts, e.g., metal acetates, to the porphycene compounds in acid medium, such as glacial acetic acid. Demetallation occurs when the metal complex is reacted with concentrated sulfuric acid at room temperature with stirring. Hydrogen ions displace the metal atom during the demetallation reaction (Buchler, J. W. in Smith, K. M. (Ed): "Porphyrin and Metalloporphyrin", Elsevier, Amsterdam, 1975; Buchler, I.

W. in Dolphin, D. (Ed), "The Porphyrin," Vol. I, Academic Press, New York, 1978; Dorough et al., J. Am. Chem. Soc., 1951, 73:4315).

The invention also includes pharmaceutically acceptable acid and base addition salts of the porphycene compounds which may be prepared by the known addition of acids such as HCl, HBr, $H_2SO_4$, $H_3PO_4$, malic acid, tartaric acid, maleic acid, fumaric acid, etc. Base addition salts are prepared by the addition of alkali and alkaline earth metal salts such as sodium, potassium, calcium and magnesium carbonates, bicarbonates, sulfates, phosphates, etc. as well as by addition of ammonia, amines, preferably primary, secondary and tertiary $C_{1-6}$ alkyl amines, amino acids, etc. Any conventional acid or base addition salt which is pharmaceutically acceptable is considered to be within the scope of the present invention.

The porphycene compounds of the present invention may be formulated as therapeutic formulations for administration to patients in need of photodynamic therapy.

Therapeutic Formulations

Therapeutic compositions containing the compounds of the present invention include liposome or microvesicle preparations, dispersions, solutions for parenteral injection, etc. and including topical dermatological preparations.

Parenteral Solutions

The photoactivatable porphycene dyes generally are used with additional solvents and adjuvants to prepare solutions suitable for intravenous injection. A number of solvents and co-solvents that are miscible with water and suitable surfactants can be used to achieve solutions for parenteral use. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laureate, palmirate, stearate, and oleate, polyoxyethylated vegetable oil, sorbitan monopalmitate, 2-pyrrolidone; N-methyl-2-pyrrolidine; N-ethyl-1-pyrrolidine; tetrahydrofurfuryl alcohol, TWEEN 80 and dimethyl isosorbide. Dimethyl isosorbide (ARLASOLVE® DMI, ICI Specialty Chemicals) has the advantage of being both water- and oil-soluble. Additionally, dimethyl isosorbide may be readily gelled with a gelling agent to produce gel formulations with, for example, 4% KLUCEL® (Hercules).

Other additives may be necessary to enhance or maintain chemical stability and physiological suitability. Examples are antioxidants, chelating agents, inert gases, buffers and isotonicifiers.

Examples of antioxidants and typical concentration ranges include acetone sodium bisulfite (0.1–0.8%), ascorbic acid (0.05–1.0%), monothioglycerol (0.1–1.0%), potassium metabisulfite (0.05–0.1%), propyl gallate (0.02%), sodium bisulfite (0.01–1.0%), sodium formaldehyde sulfoxylate (0.03–0.1%), sodium metabisulfite (0.02–0.25%), sodium sulfite (0.01–0.1%), sodium thioglycolate (0.05–0.1%).

Examples of chelating/complexing agents and typical concentration ranges include edetate sodium (0.005–0.1%), edetate calcium disodium (0.005%–0.01%), gentisic acid ethanolamide (1.0%–2.0%), niacinamide (1.0%–2.5%), sodium citrate (0.01%–2.5%), citric acid (0.001%–1.0%).

Examples of inert gases are nitrogen and carbon dioxide.

Buffers are used primarily to stabilize a solution against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area.

Examples of such buffer systems include the following acids: acetic, adipic, ascorbic, benzoic, citric, glycine, lactic, tartaric, hydrochloric, phosphoric, sulfuric, carbonic and bicarbonic; and their corresponding salts such as: potassium, sodium, magnesium, calcium and diethanolamine salts.

Osmoticity is of great importance and hypotonic solutions usually have their tonicity adjusted by the addition of salts such as sodium chloride, potassium chloride, magnesium chloride and calcium chloride and sugars such as dextrose, lactose, mannitol and sorbitol.

When the solution will be dispensed from multiple dose containers, antimicrobial agents in bacteriostatic or fungistatic concentrations must be added. Among the compounds and concentrations most frequently employed are phenylmercuric acid (0.002–0.01%), thimerosal (0.01%), benzethonium chloride (0.01%), benzalkonium chloride (0.01%), phenol or cresol (0.5%), chlorbutanol (0.5%), benzyl alcohol (2.0%), methyl p-hydroxybenzoate (0.18%), and propyl p-hydroxybenzoate (0.02%).

After the solution of the porphycene with its solvents and additives has been compounded, the solution is generally filtered to remove particulate matter above 24 µm in size and a further step eliminating particulate matter down to 0.2 µm can eliminate microorganisms and accomplish cold sterilization. The solution is filled under aseptic conditions. The final solution can be additionally sterilized in its final container by thermal methods such as autoclaving or non-thermal methods such as ionizing radiation. The process of freeze drying (lyophilization) can be employed to avoid adverse thermal and oxidative decomposition and provide enhanced stability and improved solubility.

Topical Formulations

The porphycene compounds of the present invention may be formulated for topical application in penetrating solvents or in the form of a lotion, cream, ointment or gel containing a sufficient amount of the porphycene compound to be effective for PDT therapy.

Suitable penetrating solvents are solvents for the porphycene compound which will enhance percutaneous penetration of the porphycene compound. Solvents which have this property include dimethyl sulfoxide, dimethyl acetamide, dimethylformamide, 1-methyl-2-pyrrolidone, diisopropyladipate, diethyltoluamide and to a lesser extent propylene glycol. Additional solvents include substituted azacycloalkan-2-ones having from 5 to 7 carbons in the cycloalkyl group such as 1-dodecylazacycloheptan-2-one (AZONE) and other azacycloalkan-2-ones such as described in U.S. Pat. No. 3,989,816 incorporated herein by reference.

Also included are N-bis-azocyclopentan-2-onyl alkanes described in U.S. Pat. No. 3,989,815 (hereby incorporated by reference), 1-substituted azacyclopentan-2-ones described in U.S. Pat. No. 3,991,203 (hereby incorporated by reference) and water-soluble tertiary amine oxides described in U.S. Pat. No. 4,411,893 (hereby incorporated by reference).

The topical formulations contain a sufficient amount of the porphycene compound to be effective in PDT therapy. Generally, concentrations in the range of 0.001 to 5 wt. %, preferably from about 1 to 5 wt. %, may be used. Typical lotion and cream formulations are shown below.

Additional topical formulations which may be used in conjunction with the porphycene compounds of the present invention are disclosed in U.S. Pat. No. 3,592,930 and U.S. Pat. No. 4,017,615 (hereby incorporated by reference).

Topical formulations may be prepared in gel form by combining the porphycene with a solvent such as alcohol, dimethyl sulfoxide, propylene carbonate, diethyltoluamide (DEET), diisopropyl adipate (DIPA), etc. and adding a gelling agent. A preferred gelling agent is fumed silica (CAB-0-SILO®, Cabot Corp., Tuscola, Ill.), and particularly grade M-5. The gelling agent is generally used in amounts of about 5–12 wt % to obtain a gel with the desired viscosity. Obviously, gels containing more or less gelling agent will have slightly higher or lower viscosity. One skilled in the art can readily obtain the desired gel viscosity by adjusting the concentration of gelling agent. Additives, such as cosolvents and/or surfactants, frequently improve the gel properties and may be added as desired. Suitable cosolvents/surfactants include propylene glycol and glycerine. The additives may be incorporated into the gel by mechanically mixing the additives into a mixture of solvent and gelling agent.

Liposome or Microvesicle Preparations

Liposomes and methods of preparing liposomes are known and are described for example in U.S. Pat. No. 4,452,747 and U.S. Pat. No. 4,448,765 incorporated herein by reference. Liposomes are microvesicles which encapsulate a liquid within lipid or polymeric membranes. The porphycene compounds of the present invention may be incorporated into liposome microvesicles and used in this form for both topical and parenteral application. Topical and parenteral liposome preparations are known in the art. Sonified unilamellar liposomes made from certain unsaturated lipids are known stable carriers for some of the porphycenes of the invention.

U.S. Pat. No. 4,837,028 discloses injectable liposome formulations having enhanced circulation time. The liposomes have a size of about 0.08–0.5 microns, contain at least 50 mole % of a membrane rigidifying component such as sphingomyelin and further contain about 5–15 mole % ganglioside $G_{M1}$. Liposome preparations for encapsulating sparingly soluble pharmaceutical compounds are disclosed in U.S. Pat. No. 4,721,612. The specification of these U.S. patents is incorporated herein by reference.

After administration of a therapeutically effective amount of one or more of the porphycene compounds in the pharmaceutical composition or preparation, to a patient having a treatable condition such as a solid tumor (cancer) or psoriasis, for example, the patients affected body area is exposed to a therapeutically sufficient amount of light having an appropriate wavelength for absorption by the particular porphycene compound used. Suitable wavelengths are generally from about 600 to about 900 nm, preferably from about 600 to about 700 nm. Irradiation of the accumulated porphycene usually generates singlet oxygen which is thought to be the actual lethal species responsible for destruction of the neoplastic cells.

Photodynamic therapy using the porphycene compounds of the present invention has a number of advantages. The porphycene compound itself is minimally toxic in the unexcited state. Each porphycene molecule can be repeatedly photoactivated and leads 40–60% of each time to cell-lethal events; that is, the generation of singlet molecular oxygen. The half-life of singlet molecular oxygen is approximately four microseconds in water at room temperature. The target cell is therefore affected with minor opportunity for migration of the lethal singlet molecular oxygen to neighboring healthy tissue cells. Preferably, the singlet oxygen molecules rupture chemical bonds in the target cell wall or mitochondria resulting in destruction of the target cell. Destruction of target cell tissue commences promptly upon irradiation of the porphycene compounds. Indirect target cell death can also result from destruction of the tumor vascular system with concomitant restriction of oxygen supply.

Photodynamic therapy using the compounds of the present invention is therefore selective and minimally toxic to healthy tissue. Singlet oxygen molecules produced which do not react rapidly decay to harmless ground state oxygen molecules.

A variety of phototherapy and irradiation methodologies are known to those skilled in the art and can be used with the novel porphycene compounds of the present invention. The time and duration of therapy and repetition of the irradiation treatment can be selected by the therapist (physician or radiologist) according to known photodynamic therapy criteria. The dosage of the porphycene compound may be varied according to the size and location of the target tissues which are to be destroyed and the method of administration. Generally, the dosage will be in the range of 0.05–10 mg of porphycene compound per kilogram of body weight, more preferably in the range of 0.1–5.0 mg/kg.

Irradiation generally takes place not less than two minutes nor more than four days after parenteral administration of the porphycene compound. Usually, phototherapy is begun approximately from about 5 minutes to about 24 hours after systemic administration for the tetrakis(alkoxyalkyl) porphycenes. With topically administered dye, radiation may commence as soon as 3 minutes after dye application for treatment of psoriasis, genital warts, bacterial infections, etc., but radiation up to 24 hours after due administration may be preferred according to individual dye incorporation properties. Exposure to non-therapeutic light sources should be avoided immediately following phototherapy to minimize light toxicity. Appropriate draping of the patient can be used to limit the area affected by phototherapy.

Light sources which are appropriate for use are well known in the art and may vary from non-coherent light sources with appropriate filters to lasers. As noted above, preferred wavelengths are from 600 to 900 nm, preferably from about 600 to about 700 nm. The total amount of light which is applied to the affected area will vary with the method used and the location of the tumor or topical lesion. Generally, the amount of light is in the range of about 10 to 300 $J\cdot cm^2$ preferably in the range of 20 to 200 $J\cdot cm^2$.

Having generally described this invention, a further understanding can be obtained by reference to certain specific examples which are provided herein for purposes of illustration only and are not intended to be limiting unless otherwise specified. Procedures which are constructively reduced to practice herein are described in the present tense and procedures which have been carried out in the laboratory are set forth in the past tense.

EXAMPLES

Example 1

9-(N-Boc-4-aminobutyroxy)-2,7,12,17-tetrakis-(methoxyethyl) porphycene($PbO_2$ method)

A solution of 108 mg (0.2 mmol) 2,7,12,17-tetrakis-(methoxyethyl) porphycene and 0.5 g N-Boc-4-aminobutyric acid in 20 ml dichloromethane was combined with 134 mg (0.6 mmol) $PbO_2$ and stirred for 8–10 weeks at room temperature. The mixture was then poured into 100 ml water and extracted with 50 ml dichloromethane. After washing the organic phase twice with 50 ml of 5% aqueous sodium hydrogencarbonate and twice with water, the separated organic layer was evaporated under vacuum. The residue was chromatographed with dichloromethane/ethyl acetate (1:1) on silica gel (column 15×4 cm). The first eluted fraction consisted of unchanged tetrakis(methoxyethyl)porphycene, crystallized from dichloromethane/methanol affording 27 mg. Following evaporation of the solvent and crystallization the residue of the next large fraction from dichloromethane/n-hexane, the title compound was obtained in the form of small, blue needles having a melting point of 133°–134° C. Yield: 47 mg, 31% (based on recovered TMPn: 42%).

The synthesis of the needed starting material 9-acetoxy-tetrakis (methoxyethyl)porphycene is described in U.S. Pat. No. 5,179,120 incorporated herein by reference.

Example 2

9-Hydroxy-2,7,12,17-tetrakis-(methoxyethyl)porphycene 120 mg (0.2 mmol) 9-acetoxy-2,7,12,17-tetrakis (methoxyethyl)porphycene were dissolved in 150 ml of dry tetrahydrofuran and 15 ml of absolute methanol. While stirring at room temperature, 162 mg (3 mmol) sodium methoxide were added at once. The blue-green mixture was vigorously stirred for one minute, then diluted with 150 ml diethyl ether, extracted once with ice-cold 5% aqueous sodium chloride and twice with water. Following drying the separated organic phase over anhydrous sodium sulfate, the solvent was evaporated under vacuum and the residue was recrystallized from tetrahydrofuran/n-hexane. The title compound was obtained in the form of small, blue needles which melt at 204°–206° C. with decomposition. Yield: 95 mg (85%).

Example 3

9-Methoxy-2,7,12,17-tetrakis-(methoxyethyl)porphycene

A solution of 56 mg (0.1 mmol) 9-hydroxy-tetrakis-(methoxyethyl) porphycene in 50 ml tetrahydrofuran was combined with 20 ml of 10% aqueous sodium hydroxide and vigorously stirred for 5 minutes at room temperature. The mixture was treated with 5 ml dimethylsulfate and stirred for an additional two hours. After washing the mixture thrice with 100 ml of 5% aqueous sodium chloride, the separated organic layer was evaporated under vacuum. The blue residue was chromatographed with dichloromethane/ethyl acetate (1:1) on silica gel (column 20×4 cm). Following evaporation of the solvent and crystallization of the residue of the main fraction from $CH_2Cl_2$/n-hexane, the title compound was obtained in the form of small, blue needles having a melting point of 121°–123° C. Yield: 36 mg (64%).

Example 4

9-(N-Boc-Glycinoxy)2,7,12,17-tetrakis-(methoxyethyl)-porphycene 56 mg (0.1 mmol)9-hydroxy-tetrakis(methoxyethyl)-porphycene were dissolved in 5 ml absolute tetrahydrofuran and 3 ml absolute pyridine. The stirred solution was combined with 175 mg (1 mmol) N-Boc-glycine and a solution of 206 mg (1 mmol) dicyclohexylcarbodiimide (DCC) in 5 ml absolute tetrahydrofuran. After stirring for an additional two hours at room temperature, insoluble material (DCU) was filtered off and washed with diethyl ether. Following washing of the combined organic solutions twice with 10% sulfuric acid, once with water and 5% aqueous sodium hydrogencarbonate, the separated organic layer was evaporated under vacuum. The blue residue was chromatographed with dichloromethane/ethyl acetate (5:1) on silica gel (column 20×4 cm). For the complete elution and separation of the dicyclohexylurea (DCU), it was necessary to change slowly the composition of the solvent mixture from 5:1 to 2:1. Following elution of the porphycene main fraction, evaporation of the solvent and crystallization of the residue from $CH_2Cl_2$/n-hexane, the title compound was obtained in the form of blue, fibrous needles having a melting point of 147°–148° C. Yield: 61.5 mg (86%).

Example 5

9-Amino-2,7,12,17-tetrakis(methoxyethyl)porphycene 542 mg (1 mmol) tetrakis(methoxyethyl)porphycene were dissolved in 250 ml dichloromethane and 350 ml glacial acetic acid and combined with 680 mg (4 mmol) of finely ground $AgNO_3$. The stirred suspension was heated with reflux for 20–25 minutes. The reaction can be followed by means of thin layer chromatography (TLC: dichloromethane/ethyl acetate (3:1), silica gel). After cooling to room temperature, the insoluble material was removed and the solution was washed two times with water. The organic layer was brought to pH 6–6.5 with ice-cold 5% aqueous sodium hydroxide and finally washed with water. The raw product 9-nitro-tetrakis(methoxyethyl) porphycene was left in 300 ml dichloromethane, each combined with a solution of 40 g (1 mol) sodium hydroxide in 200 ml water and 36 g (0.2 mol) sodium dithionite in 200 ml water. The mixture was refluxed under vigorously stirring for 45 minutes (TLC: dichloromethane/ethyl acetate (3:1), silica gel). After cooling to room temperature and separating the two phases, the organic layer was washed three times with water and the organic solvent was evaporated under vacuum. The blue-green residue was recrystallized from dichloromethane/methanol to yield 468 mg (84%) 9-amino-tetrakis(methoxyethyl)porphycene in the form of small, dark violet needles having a melting point of 193°–195° C.

Example 6

9-(Glutaric methylesteramide)-2,7,12,17-tetrakis-(methoxyethyl)porphycene 468 mg (0.84 mmol)9-amino-tetrakis(methoxyethyl)-porphycene were dissolved in 60 ml dry tetrahydrofuran and 15 ml dry pyridine. To the stirred solution was added at room temperature dropwise in 10 minutes a solution of 1 ml (7 mmol) glutaric methylester acid chloride in 40 ml dry tetrahydrofuran. The mixture was stirred for an additional one hour at room temperature, diluted with dichloromethane, cooled to 0° C. and treated with ice chilled water. The solvent mixture was washed twice with 10% sulfuric acid, twice with water and once with 5% aqueous sodium hydrogencarbonate. After evaporation of the solvent of the separated organic layer, the residue was chromatographed with dichloromethane/ethyl acetate/methanol (4:4:1) on silica gel (column 30×4 cm). Following evaporation of the solvent under vacuum and recrystallization of the residue of the main fraction from dichloromethane/hexane, the title compound 9-(glutaric methylesteramide)tetrakis-(methoxyethyl) porphycene was obtained in the form of violet needles having a melting point of 146°–147° C. Yield: 534 mg (92%).

Example 7

9-Glutaramide-2,7,12,17-tetrakis(methoxyethyl)porphycene 68.5 mg (0.1 mmol) 9-glutaric methylesteramide-tetrakis(methoxyethyl)porphycene were dissolved in 20 ml tetrahydrofuran, combined with 20 ml methanol and 10 ml of 4N aqueous sodium hydroxide were added dropwise within 5 minutes while stirring at room temperature. The reaction was stirred for an additional hour, neutralized and then precipitated under acidic conditions with the complete addition of ice-cold 150 ml 5% acetic acid. The suspension was stirred for an additional hour, the flaky precipitate was filtered off, washed with water and dried. For purification, the blue residue was redissolved in dichloromethane, filtered and recrystallized after addition of n-hexane. The title compound was obtained in the form of small, blue needles having a melting point of 171°–173° C. Yield: 56 mg (83%).

Syntheses with carotenoids described below were carried out under protection from light, and under a protective gas (argon) atmosphere. All solvents used were treated to remove water and other impurities, and were saturated with argon. For the chromatographic separations, high elution rate and a short contact time (flash chromatography) was used.

Example 8

4-(Methoxycarbonyl)benzyl triphenylphosphonium bromide 3.44 g (13 mmol) Triphenylphosphine was dissolved in 100 ml dry toluene, in a 250 ml flask with an argon feed. 3 g (13 mmol) 4-(bromomethyl)benzoic acid methyl ester was added, and the mixture was heated 2 hr at reflux, with stirring. The white phosphonium salt which precipitated was separated out from the cooled mixture, washed with absolute toluene, and dried in a vacuum. The fine crystals melted at 251°–252° C. Yield: 5.85 g (91%).

Example 9

4-(β-Apo-7'-carotenyl)benzoic acid methyl ester 860 mg (1.8 mmol) 4-(methoxycarbonyl)benzyl triphenylphosphonium bromide, 173 mg (3.2 mmol) sodium methanolate, and 500 mg (1.2 mmol) β-apo-8'-carotenal were dissolved in 25 ml absolute toluene. The dark-colored liquid was heated 3 hr at reflux. The course of the reaction was monitored by thin layer chromatography (silica gel with dichloromethane:ethyl acetate 5:1); additionally, there were added 500 mg (1 mmol) of the phosphonium bromide and 100 mg (1.8 mmol) sodium methanolate. After an additional 4–5 hr under reflux, the completely reacted mixture was cooled, diluted with 150 ml dichloromethane, and extracted 3 times with 150 ml aliquots of water. The organic phase was dried over magnesium sulfate, the solvent was removed under vacuum, and the reddish-brown residue was chromatographed with dichloromethane:ethyl acetate 5:1 over silica gel, under inert conditions (column: 15×4 cm). Following a red forerun, the orange main fraction was eluted, from which 405 mg (61%) of the carotenoid methyl ester was obtained following evaporation of eluent under vacuum and recrystallization from dichloromethane/hexane. The red crystals had a melting point of 168°–170° C.

Example 10

4-(β-Apo-7'-carotenyl)benzoic acid 6 ml 5N sodium hydroxide was added to a solution of 220 mg (0.4 mmol) 4-(β-Apo-7'-carotenyl)-benzoic acid methyl ester in 40 ml tetrahydrofuran and 10 ml methanol, and the mixture was stirred 12 hr at room temperature, under light protection and under an argon atmosphere. The mixture was cooled, brought to pH 1–2 with 5% sulfuric acid, and extracted 3 times with dichloromethane. The combined organic phases were washed twice with water, dried over sodium sulfate, and vacuum distilled to remove the solvent. The yield of orangeish-red carotenoid carboxylic acid was 200 mg (92%).

Recrystallization from dichloromethane:hexane yielded fine, red crystals which melted at 230°–232° C.

Example 11

4-(β-Apo-7'-carotenyl)benzoyl chloride 80 mg (0.15 mmol) 4-(β-Apo-7'-carotenyl)benzoic acid was dissolved in 4 ml absolute toluene and 2 ml absolute pyridine. 55 µl (0.75 mmol) Thionyl chloride in 3 ml absolute toluene was added dropwise to this mixture, and stirring was continued 10–12 min at room temperature. Then the solvent mixture and excess thionyl chloride were removed by water flow aspiration, over a water bath at 18°–22° C., and the remaining reddish-brown acid chloride was absorbed in 5 ml absolute tetrahydrofuran.

Example 12

9-(4-(β-Apo-7'-carotenyl)benzoyloxy)-2,7,12,17-tetrakis (methoxyethyl)porphycene The acid chloride solution of Example 11 was added dropwise to a solution of 56 mg (0.1 mmol) 9-hydroxytetrakis(methoxyethyl)porphycene in 5 ml tetrahydrofuran and 3 ml absolute pyridine, and the mixture was stirred an additional 1 hr at room temperature. The mixture was diluted with 100 ml dichloromethane, hydrolyzed with ice water, and extracted twice with fresh portions of ice-cold 10% sulfuric acid. After washing the organic phase with 5% sodium hydrogen carbonate solution and then water, the solvent was removed under vacuum. The blackish-brown residue obtained was chromatographed with dichloromethane:ethyl acetate 5:1 over silica gel, under inert conditions (column: 20×4 cm). Following an orange forerun, the reddish-brown product fraction was eluted, from which 56 mg (52%) of the blackish-brown microcrystalline 9-O-carotenoporphycene was obtained, after evaporation of the eluent and recrystallization from dichloromethane:methanol. The substance was particularly sensitive to light and oxygen when in solution and melted at 154°–156°C.

Example 13

9-(4-[β-Apo-7'-carotenyl) benzamido)-2,7,12,17-tetrakis(methoxyethyl)porphycene The solution of the carotenyl acid chloride of Example 11 was added dropwise to a solution of 56 mg (0.1 mmol) 9-amino-tetrakis (methoxyethyl)porphycene in 5 ml absolute tetrahydrofuran and 3 ml absolute pyridine, and the mixture was stirred an additional 1 hr at room temperature. The mixture was diluted with 100 ml dichloromethane, hydrolyzed with ice water, and extracted twice with ice-cold 10% sulfuric acid. After washing the organic phase with 5% sodium hydrogen carbonate solution and then water, the solvent was removed under vacuum. The blackish-brown residue obtained was chromatographed with dichloromethane:ethyl acetate 5:1 over silica gel, under inert conditions (column: 20×4 cm). Following an orange forerun, the brown product fraction was eluted, from which 60 mg (56%) of the blackish-brown microcrystalline 9-O-carotenamidoporphycene was obtained, after evaporation of the eluent and recrystallization from dichloromethane:methanol. The substance was particularly sensitive to light and oxygen when in solution and melted at 174°–176° C.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A porphycene of the formula:

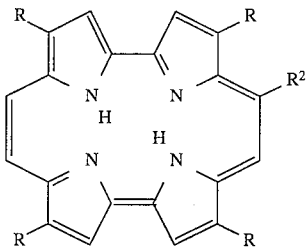

wherein each R is, independently, —$(CH_2)_n$—X, n=1–10, X is $OR^1$, and $R^1$ is alkyl, aralkyl or aryl;

$R^2$ is (1) hydroxy, alkoxy or $OCOR^3$, wherein $R^3$ is —$(CH_2)_m$—Y, m=1–10 and Y is:
 (a) hydrogen or halogen,
 (b) $C(O)OR^4$, wherein $R^4$ is hydrogen, alkyl, aryl, aralkyl, cycloalkyl or cycloalkylalkyl,
 (c) $NR^5R^6$ wherein $R^5$ and $R^6$, independently, are hydrogen, alkyl, aryl, aralkyl, cycloalkyl or cycloalkylalkyl,
 (d) $NR^4R^5R^{6+}A^{31}$, wherein $A^{31}$ is an anion and $R^4$, $R^5$ and $R^6$ are as defined above,
 (e) $NHC(O)OR^4$, wherein $R^4$ is as defined above; or $R^2$ is (2):
 $OC(O)R^7$, wherein $R^7$ is substituted or unsubstituted aryl or —$CHR^8$=$CHR^9$—$R^{10}$, $R^8$ and $R^9$ are, independently, hydrogen or $C_{1-6}$ alkyl, and $R^{10}$ is alkyl, aryl, aralkyl, cycloalkyl or cycloalkylalkyl; or $R^2$ is (3):
 (a) $NR^{11}R^{12}$, wherein $R^{11}$ and $R^{12}$ independently, are hydrogen, alkyl, aryl, aralkyl, cycloalkyl or cycloalkylalkyl, (b) NHCO—$(CH_2)_p$13 Z, wherein p=1–10 and Z is H, OH, $NR^{11}R^{12}$, $C(O)OR^4$, $OC(O)R^4$, $C(O)NHR^4$ or $NHC(O)OR^4$, wherein $R^4$, $R^{11}$ and $R^{12}$ are as defined above; or $R^2$ is (4):

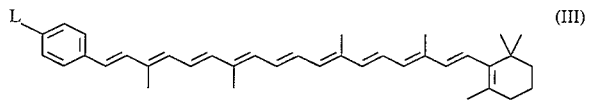

wherein L is —OC(O)— or —NHC(O)—; salts or metal complexes thereof, provided that said porphycene is not 9-acetoxy-2,7,12,17-tetrakis (methoxyethyl) porphycene.

2. The porphycene of claim 1, where $R^1$ is $C_{1-6}$ alkyl and n=1–6.

3. The porphycene of claim 1, wherein $R^2$ is hydroxy or alkoxy.

4. The porphycene of claim 1, wherein $R^2$ is —$OCOR^3$, $R^3$ is $(CH_2)_m$—Y, m=1–10 and Y is hydrogen or halogen.

5. The porphycene of claim 1, wherein $R^2$ is —$OCOR^3$, R is $(CH_2)_m$—Y, m=1–6, Y is a $COOR^4$ and $R^4$, is $C_{1-6}$ alkyl.

6. The porphycene of claim 1, wherein $R^2$ is —$OCOR^3$, R is $(CH_2)_m$—Y, m=1–6, Y is $NR^5R^4$ or $NR^4R^5R^{6+}A_-$ and $R^4$, $R^5$ and $R^6$ are $C_{1-6}$ alkyl.

7. The porphycene of claim 1, wherein $R^2$ is —$OCOR^3$, $R^3$ is $(CH_2)_m$—Y, m=1–6, Y is NH—$C(O)OR^4$, and $R^4$ is $C_{1-6}$ alkyl.

8. The porphycene of claim 1, wherein $R^2$ is $OC(O)R^7$, $R^7$ is phenyl or —$CHR^8$=$CHR^9$—$R^{10}$, $R^8$ and $R^9$ are hydrogen or $C_{1-6}$ alkyl, and $R^{10}$ is $C_{1-6}$ alkyl or phenyl.

9. The porphycene of claim 1, wherein $R^2$ is $NR^{11}R^{12}$, wherein $R^{11}$ and $R^{12}$, independently, are hydrogen or $C_{1-6}$ alkyl.

10. The porphycene of claim 1, wherein $R^2$ is —$NHCO(CH_2)_p$—Z or —$NH(CH_2)_{p+1}$—Z, p=1–6 and Z is H, OH, $OCOR^4$ or $C(O)OR^4$, wherein $R^4$ is H or $C_{1-6}$ alkyl.

11. The porphycene of claim 10, wherein $R^2$ is —$NHCO(CH_2)_p$—Z, p=1 and Z is H.

12. The porphycene of claim 1, wherein $R^2$ is —$NHCO(CH_2)_p$—Z or —$NH(CH_2)_{p+1}$—Z, p=1–6 and Z is $NH_2$ or $NHC(O)OR^4$, wherein $R^4$ is H or $C_{1-6}$ alkyl.

13. The porphycene of claim 1, wherein $R^2$ has formula III shown below:

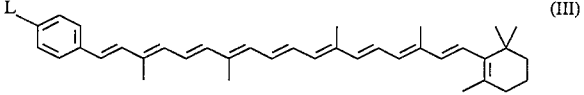

wherein L is —OC(O)— or —NHC(O)—.

14. A pharmaceutical composition comprising an effective amount of the porphycene of claim 1 and a pharmaceutically acceptable carrier.

15. A method of photodynamic therapy, comprising and administering to a patient in need thereof an effective amount of the porphycene of claim 1.

16. The porphycene of claim 1, wherein $R^2$ has formula (III) and L is —OC(O)—.

17. The porphycene of claim 1, wherein $R^2$ has formula (III) and L is —NHC(O)—.

18. The porphycene of claim 1, wherein R is $CH_2CH_2OCH_3$.

* * * * *